US 9,717,863 B2

(12) United States Patent
Davies et al.

(10) Patent No.: US 9,717,863 B2
(45) Date of Patent: Aug. 1, 2017

(54) DISPENSE INTERFACE WITH LOCKOUT ELEMENT

(75) Inventors: James Alexander Davies, Warwickshire (GB); Simon Lewis Bilton, Warwickshire (GB); David Moore, Leicestershire (GB); Steven Wimpenny, Warwickshire (GB); Christopher Nigel Langley, Warwickshire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 49 days.

(21) Appl. No.: 14/113,392

(22) PCT Filed: Apr. 26, 2012

(86) PCT No.: PCT/EP2012/057680
§ 371 (c)(1),
(2), (4) Date: Apr. 30, 2014

(87) PCT Pub. No.: WO2012/146670
PCT Pub. Date: Nov. 1, 2012

(65) Prior Publication Data
US 2014/0303555 A1    Oct. 9, 2014

Related U.S. Application Data

(60) Provisional application No. 61/480,063, filed on Apr. 28, 2011.

(30) Foreign Application Priority Data

Jul. 8, 2011   (EP) .................................... 11173266

(51) Int. Cl.
A61M 5/50    (2006.01)
A61M 5/34    (2006.01)
A61M 5/31    (2006.01)

(52) U.S. Cl.
CPC ................ *A61M 5/50* (2013.01); *A61M 5/34* (2013.01); *A61M 5/347* (2013.01); *A61M 2005/3118* (2013.01); *A61M 2005/3128* (2013.01)

(58) Field of Classification Search
CPC .......... A61M 5/50; A61M 5/34; A61M 5/347; A61M 2005/3118; A61M 2005/3128;
(Continued)

(56) References Cited

U.S. PATENT DOCUMENTS

2003/0153895 A1*   8/2003   Leinsing ................. 604/403
2008/0154192 A1*   6/2008   Schraga .................. 604/110
(Continued)

FOREIGN PATENT DOCUMENTS

EP      1813305       8/2007
EP      1949926       7/2008
(Continued)

OTHER PUBLICATIONS

International Search Report for Int. App. No. PCT/EP2012/057680, completed Aug. 20, 2012.

*Primary Examiner* — Bhisma Mehta
*Assistant Examiner* — Hamza Darb
(74) *Attorney, Agent, or Firm* — McDonnell Boehnen Hulbert & Berghoff LLP

(57) ABSTRACT

The invention is related to an apparatus comprising a dispense interface comprising a lockout element for use with a drug delivery device, the lockout element comprising at least one spring component removeably maintained in a respective first position such that when the dispense interface is first attached and then removed from said drug delivery device, each spring component moves into a respective second position, which respective second position (Continued)

is configured to prevent said dispense interface from being reattached to a drug delivery device.

6 Claims, 12 Drawing Sheets

(58) Field of Classification Search
CPC ...... A61M 5/2448; A61M 5/19; A61M 5/162; A61J 1/2055; A61J 1/2058
USPC ............... 604/82–92, 191, 411–415, 905
See application file for complete search history.

(56) References Cited

U.S. PATENT DOCUMENTS

| | | |
|---|---|---|
| 2008/0177238 A1 | 7/2008 | Follman et al. |
| 2009/0216212 A1* | 8/2009 | Fangrow, Jr. .................. 604/406 |

FOREIGN PATENT DOCUMENTS

| | | |
|---|---|---|
| JP | 2005-516691 | 6/2005 |
| JP | 2008-212645 | 9/2008 |
| WO | 99/44661 | 9/1999 |
| WO | 2008/083037 | 7/2008 |
| WO | 2009/154826 | 12/2009 |
| WO | 2010/053574 | 5/2010 |

* cited by examiner

DISPENSE INTERFACE WITH LOCKOUT ELEMENT

CROSS REFERENCE TO RELATED APPLICATIONS

The present application is a U.S. National Phase Application pursuant to 35 U.S.C. §371 of International Application No. PCT/EP2012/057680 filed Apr. 26, 2012, which claims priority to U.S. Provisional Patent Application No. 61/480,063 filed Apr. 28, 2011 and European Patent Application No. 11173266.5 filed Jul. 8, 2011. The entire disclosure contents of these applications are herewith incorporated by reference into the present application.

FIELD OF THE DISCLOSURE

The present patent application relates to medical devices for delivering at least two drug agents from separate reservoirs. Such drug agents may comprise a first and a second medicament. The medical device includes a dose setting mechanism for delivering the drug agents automatically or manually by the user. In particular, the present invention relates to a dispense interface with a lockout element as for example usable in such a medical drug delivery device.

The medical device can be an injector, for example a hand-held injector, especially a pen-type injector, that is an injector of the kind that provides for administration by injection of medicinal products from one or more multidose cartridges. In particular, the present invention relates to such injectors where a user may set the dose.

The drug agents may be contained in two or more multiple dose reservoirs, containers or packages, each containing independent (single drug compound) or pre-mixed (co-formulated multiple drug compounds) drug agents.

BACKGROUND

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it may be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then only combined and/or delivered to the patient during a single delivery procedure. These active agents may be administered together in a combined dose or alternatively, these active agents may be combined in a sequential manner, one after the other.

SUMMARY

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with a primary reservoir and with a secondary reservoir of medicament containing at least one drug agent. The drug dispense interface can be a type of outlet that allows the two or more medicaments to exit the system and be delivered to the patient.

The combination of compounds from separate reservoirs can be delivered to the body via a double-ended needle assembly. This provides a combination drug injection system that, from a user's perspective, achieves drug delivery in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable. Alternatively, the user can dial or set a desired dose of the secondary compound.

5. Optionally, after the second dose has been set, the device may be placed in an armed condition. The optional armed condition may be achieved by pressing and/or holding an "OK" or an "Arm" button on a control panel. The armed condition may be provided for a predefined period of time during which the device can be used to dispense the combined dose.

6. Then, the user will insert or apply the distal end of the dose dispenser (e.g. a double ended needle assembly) into the desired injection site. The dose of the combination of the primary compound and the secondary compound (and potentially a third medicament) is administered by activating an injection user interface (e.g. an injection button).

Both medicaments may be delivered via one injection needle or dose dispenser and in one injection step. This offers a convenient benefit to the user in terms of reduced user steps compared to administering two separate injections.

Delivering one or more medicaments through a dose dispenser with a dispense interface can result in the contamination of the dispense interface with traces of each medicament. This contamination may prohibit reusing the dispense interface, for example after a certain time or after a predetermined number of usages, because the purity of the delivered medicaments cannot be guaranteed. Even a user who is conscious of this problem may inadvertently try to reuse a dispense interface because he may not remember and may find it difficult or impossible to determine by inspection whether a given dispense interface has in fact been used or not.

It is therefore desirable to provide the dispense interface with a mechanism that prevents reuse of the dispense interface with a drug delivery device. This mechanism should be such that it is effective in its prevention of reuse as well as safe from manual manipulation by a user.

Thus it is an object of the invention to provide a dispense interface for use with a drug delivery device which has a lockout mechanism that prevents reusing this dispense interface after it has already been used with a drug delivery device.

This object is solved by an apparatus comprising: a dispense interface for use with a drug delivery device, the dispense interface comprising a lockout element, the lockout element comprising at least one spring component removably maintained in a respective first position such that when the dispense interface is first attached and then removed from said drug delivery device, each spring component moves into a respective second position, which respective second position is configured to prevent said dispense interface from being reattached to a drug delivery device.

The lockout element is arranged in its default state, i.e. in its first position, such that it allows attachment of the dispense interface to the drug delivery device. However, the process of attaching the dispense interface to the drug delivery device mechanically moves the lockout element such that, once the dispense interface is detached and thereby is removed from the drug delivery device, the lockout element mechanically blocks a reattachment of the dispense interface to any drug delivery device of the same or similar kind. Therefore a reuse of the dispense interface is prevented and the risk of contamination from residual drug components within the dispense interface eliminated.

To this end, the lockout element comprises at least one spring component in a first position in which it does not interfere with the attachment of the dispense interface to the drug delivery device. There may be any number of spring components. Without loss of generality, the further description will assume there to be a plurality of spring components. In this first position, the spring components are already held under tension and therefore store potential energy. Moreover, the spring components are arranged such that they are mechanically engaged by a part of the drug delivery device during the attachment of the dispense interface to the drug delivery device. This engagement moves the spring components such that they are released from their hold, thereby permitting them to change their position by virtue of their stored energy. This change of position may also comprise a change of shape of the spring components. The change of position may only affect parts of the spring component, i.e. not all parts of the spring component may have changed their location when the spring component is said to have moved from the first position to a next position. In the second position, which the spring component moves into either directly after having left the first position or after possibly having gone through one or more intermediate positions, the spring components block the re-attachment of the dispense interface to any drug delivery device of the same or similar kind. In the second position, the spring components block tubular stubs configured to receive the cartridge boss associated with each reservoir of the drug delivery device.

Elaborating on the movement of the spring components to the second position, the spring components may complete their move to the second, blocking position only after the dispense interface has been detached from the drug delivery device. In particular, the spring components may be moved to an intermediate third position, which is non-blocking, on engagement with the drug delivery device. In this third position, the spring components may be biased to move into the second position but may be prevented from doing so by the still-attached drug delivery device. When the dispense interface is detached from the drug delivery device, the spring components are released and may fully move into the blocking second position.

Attaching the dispense interface to the drug delivery device entails creating a fluid connection between the dispense interface and the reservoirs of the drug delivery device storing the medicaments to be delivered. Preferably, the dispense interface comprises a spring component for each fluid connection to a reservoir of the drug delivery device. In other words, the dispense interface preferably comprises as many spring components as it has fluid connections sockets corresponding to the cartridge bosses of the drug delivery device.

A preferred embodiment is characterized in that each spring component comprises a respective button spring, each respective button spring comprising a respective set of winged tabs. The winged tabs are preferably arranged at the circumference of the button spring and facing a direction perpendicular to the button spring. The winged tabs are preferably arranged to move radially inward when the button spring is sprung.

In another preferred embodiment, each button spring is an over-centering wing spring.

In a further preferred embodiment, each set of winged tabs comprises three winged tabs.

In yet a further preferred embodiment, each button spring is dome-shaped.

In another preferred embodiment, each winged tab of each respective set of winged tabs is configured to move radially inward when the respective button spring moves into the respective second position.

In yet another preferred embodiment, each spring component comprises a respective circlip spring. Each circlip spring is essentially ring-shaped, though it may have one or more projections in the outward or inward direction. Each circlip spring may be arranged around a respective tubular stub, wherein each tubular stub is configured to receive the cartridge boss associated with each reservoir of the drug delivery device. Each circlip spring is further configured to assume one of two positions. In the first position, the circlip spring is extended radially outwards and has a greater diameter. In this position, the circlip spring is in a strained state with internal strain acting to contract the circlip spring. In the second position, the circlip spring is contracted and has a smaller diameter.

In a further preferred embodiment, each circlip spring is maintained in a respective first diameter channel provided by the dispense interface in the respective first position. In particular, this diameter channel may be a tubular stub on the dispense interface configured for connecting to the corresponding cartridge boss of the medicament reservoir of the drug delivery device. This first diameter channel may have a diameter sufficiently large to maintain the respective circlip spring in a strained state.

In another preferred embodiment, each circlip spring is configured to be shunted forwards into a respective second diameter channel which is on a smaller diameter than the respective first diameter channel when the dispense interface is attached to said drug delivery device. Each circlip spring may be shunted forwards by being engaged by a part of the drug delivery device on the attachment of the dispense interface to the drug delivery device, in particular by a cartridge boss associated with a reservoir of the drug delivery device. Each circlip spring may be shunted forwards by being pushed on a tubular stub in the axial direction toward the dispense interface. The second diameter channel may be a part of the tubular stub with a smaller diameter than the part of the tubular stub around which the circlip spring is maintained in the position of the circlip spring before being shunted forwards, i.e. the first diameter channel.

In a preferred embodiment, each circlip spring is configured to spring inwards in the radial direction when said dispense interface is removed from said drug delivery device and thereby detached. Because the circlip spring is, after being shunted forewards, in a second diameter channel on a smaller diameter, the strain on the circlip spring from being originally in the position of greater diameter acts to contract the circlip spring to the smaller diameter. However, as long as the dispense interface is attached to the drug delivery device, the engaging parts of the drug delivery device may act to maintain the circlip spring on the first diameter, i.e. the greater diameter. Therefore the circlip spring will contract by springing inwards when the dispense interface is removed from the drug delivery device maintaining the circlip spring in the greater diameter.

In a further preferred embodiment, a portion of each circlip spring is configured to deflect sufficiently inward to shrink an effective receptive diameter to prevent said dispense interface from being reattached to a drug delivery device. This prevention may occur, in particular, through a mechanical blocking effect of the inwardly deflected portion of the circlip spring. The effective receptive diameter may be the diameter of a tubular stub configured for engaging its counter part, for example a cartridge boss of the drug delivery device, and thereby creating a fluid connection with a reservoir of the drug delivery device. There is a minimum diameter under which the effective receptive diameter must not fall in order for an attachment of the dispense interface to the drug delivery device to be possible. The inwardly deflected portion of each circlip spring may comprise a protrusion in the inward direction.

In yet a further preferred embodiment, each circlip spring is maintained in the respective first position by a respective tab. The respective tab may be held in place by a tightening force exerted by the circlip spring due to its internal strain. The respective tab may also have a small but integral connection with the circlip spring configured to be torn when the tab is forced away by the engaging part of the drug delivery device.

In a preferred embodiment, each circlip spring is configured to move into a respective locked condition upon deflection of the respective tab during the attachment of the dispense interface to said drug delivery device and subsequent detachment of the dispense interface from the drug delivery device. It may be that each circlip spring does not move upon deflection of the respective tab as long as the drug delivery device which has deflected the respective tab is in place and takes up the previous space of the respective tab and that consequently each circlip spring completes its movement into the locked condition after the dispense interface has been detached from the drug delivery device.

In another aspect, a dispense interface for use with a drug delivery device is provided. The dispense interface comprises a main outer body and an inner body positioned within at least a portion of the main outer body. The inner body may be configured for connection to a drug delivery device and defines a first inner body reservoir and a second inner body reservoir. The dispense interface further comprises a first piercing needle in fluid communication with the first inner body reservoir and positioned for piercing a first reservoir contained within a drug delivery device. A second piercing needle is provided by the inner body and in fluid communication with the second inner body reservoir and positioned for piercing a second reservoir contained with a drug delivery device. A manifold is positioned adjacent a generally flat surface of the inner body and comprises a fluid groove arrangement. A valve arrangement is positioned between the inner body and the manifold. The valve arrangement controls fluid communication of a first fluid contained in the first cartridge and a second fluid contained in the second cartridge by way of the fluid groove arrangement to a holding chamber of the inner body. The dispense interface may further comprise a lockout preventing dispense interface reuse.

BRIEF DESCRIPTION OF THE FIGURES

These as well as other advantages of various aspects of the present invention will become apparent to those of ordinary skill in the art by reading the following detailed description, with appropriate reference to the accompanying drawings, in which.

DETAILED DESCRIPTION

Figure 1:
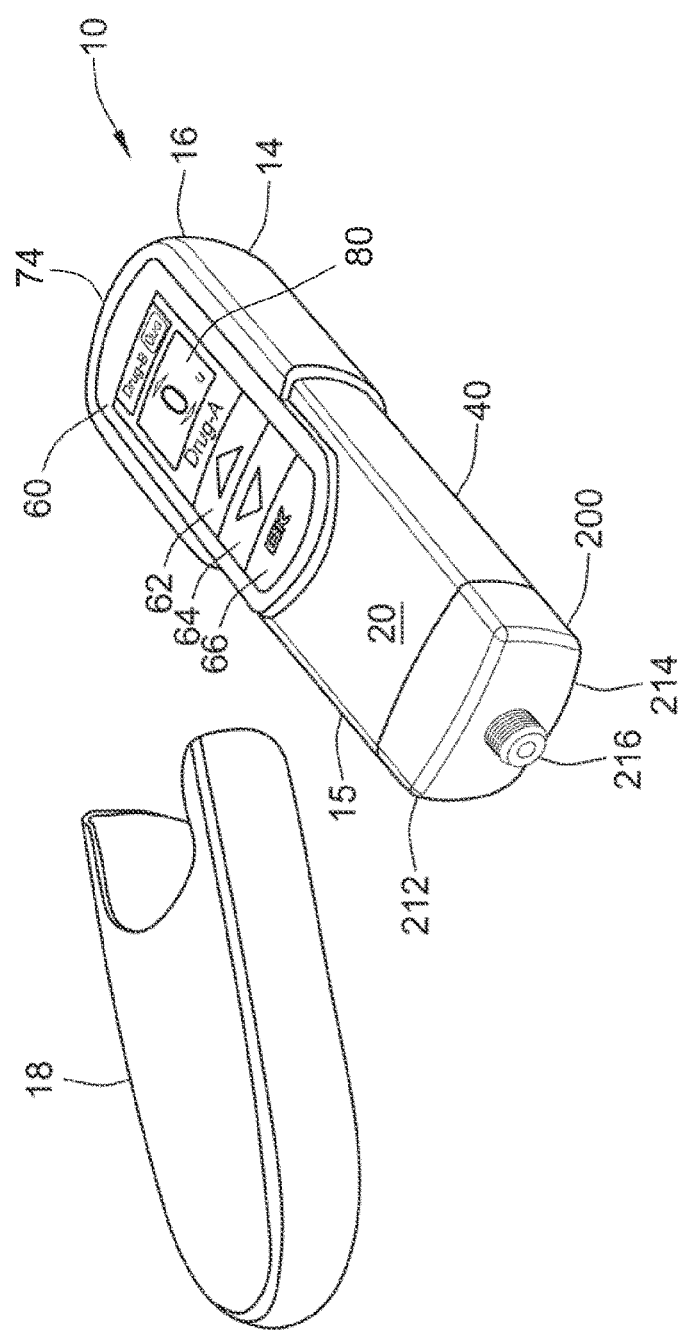
FIG. 1 illustrates a perspective view of a delivery device with an end cap of the device removed.
Figure 2:
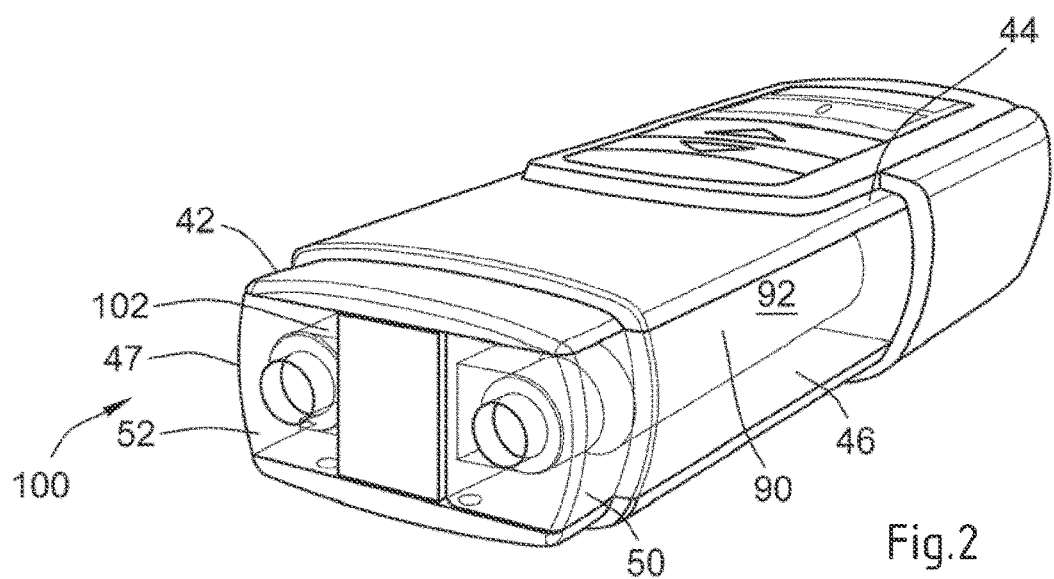
FIG. 2 illustrates a perspective view of the delivery device distal end showing the cartridge.

The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

The drive train may exert a pressure on the bung of each cartridge, respectively, in order to expel the doses of the first and second medicaments. For example, a piston rod may push the bung of a cartridge forward a pre-determined amount for a single dose of medicament. When the cartridge is empty, the piston rod is retracted completely inside the main body 14, so that the empty cartridge can be removed and a new cartridge can be inserted.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1).

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 212 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

Figure 3:
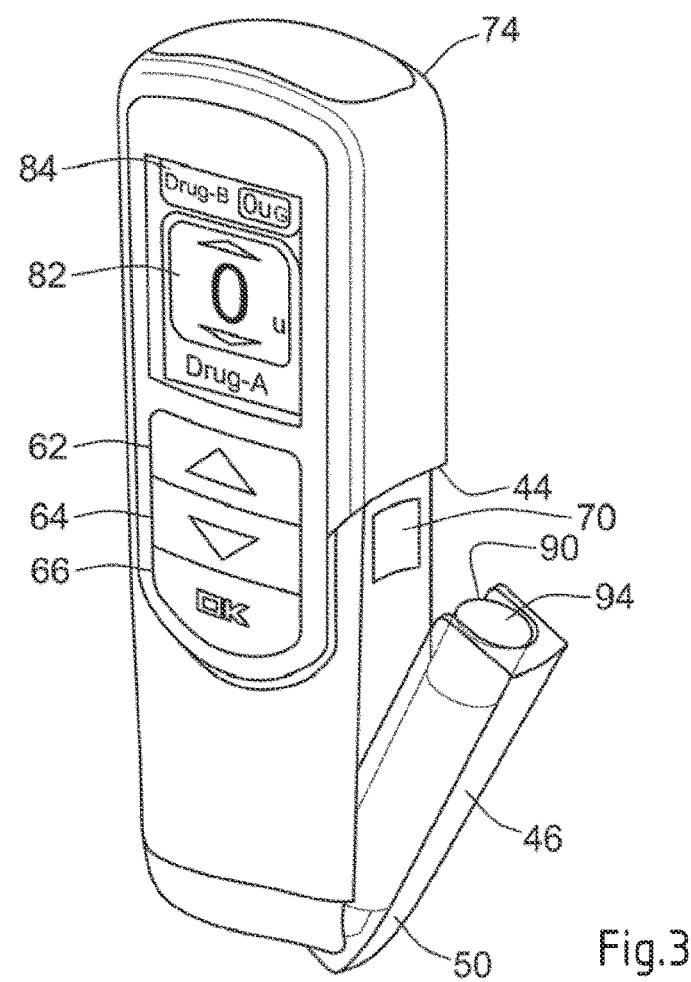
FIG. 3 illustrates a perspective view of the delivery device illustrated in FIG. 1 or 2 with one cartridge retainer in an open position.

As shown in FIG. 3, a first and a second cartridge retainer 50, 52 comprise hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
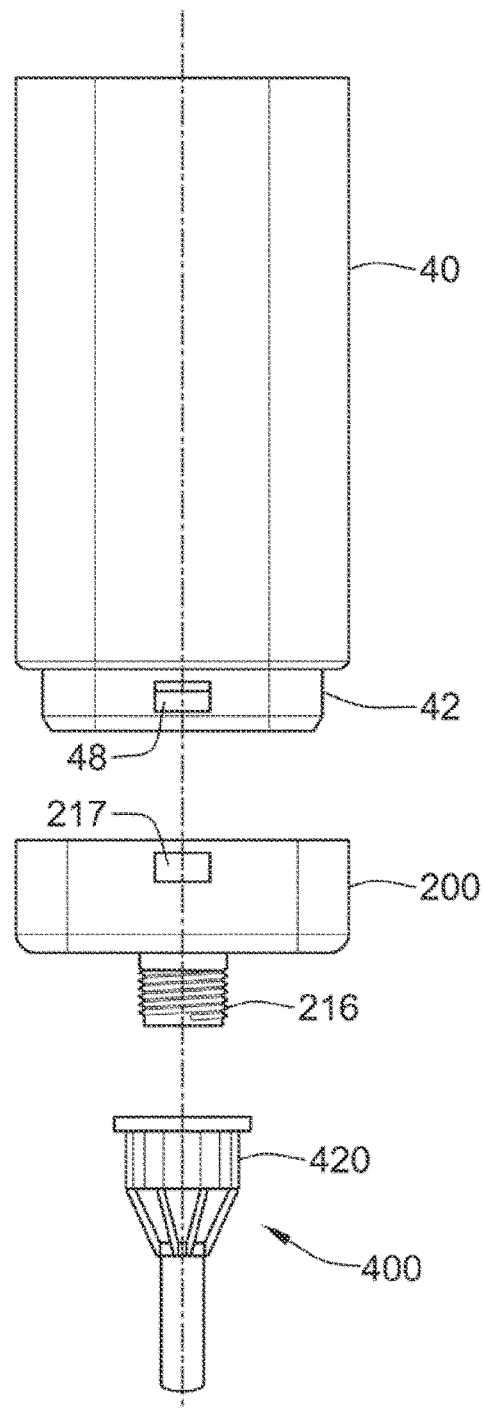
FIG. 4 illustrates a dispense interface and a dose dispenser that may be removably mounted on a distal end of the delivery device illustrated in FIG. 1.

As mentioned above when discussing FIG. 1, a dispense interface 200 is coupled to the distal end of the cartridge holder 40. FIG. 4 illustrates a flat view of the dispense interface 200 unconnected to the distal end of the cartridge holder 40. A dose dispenser or needle assembly 400 that may be used with the interface 200 is also illustrated and is provided in a protective outer cap 420.

Figure 5:
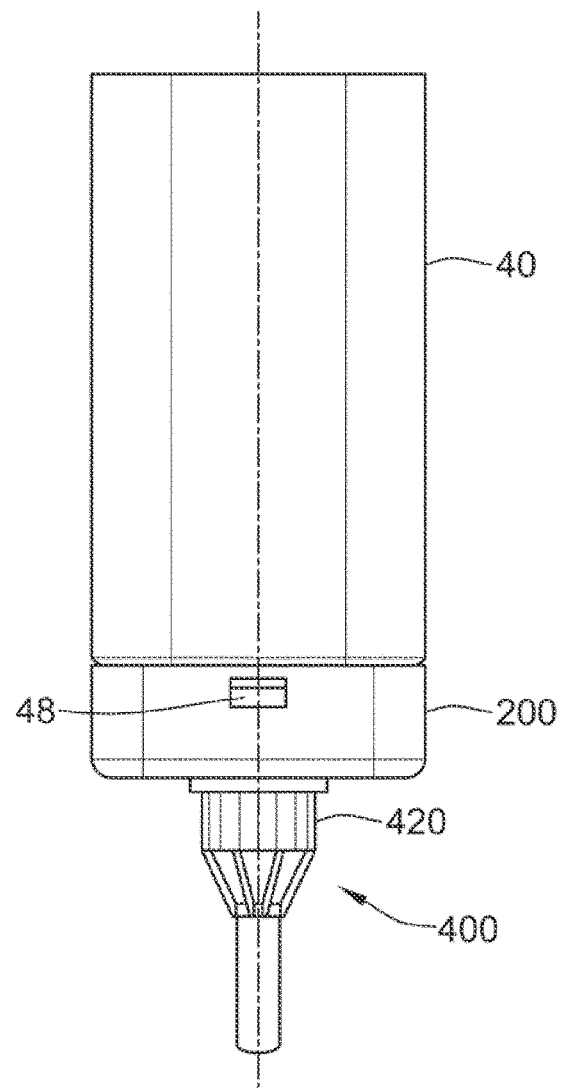
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
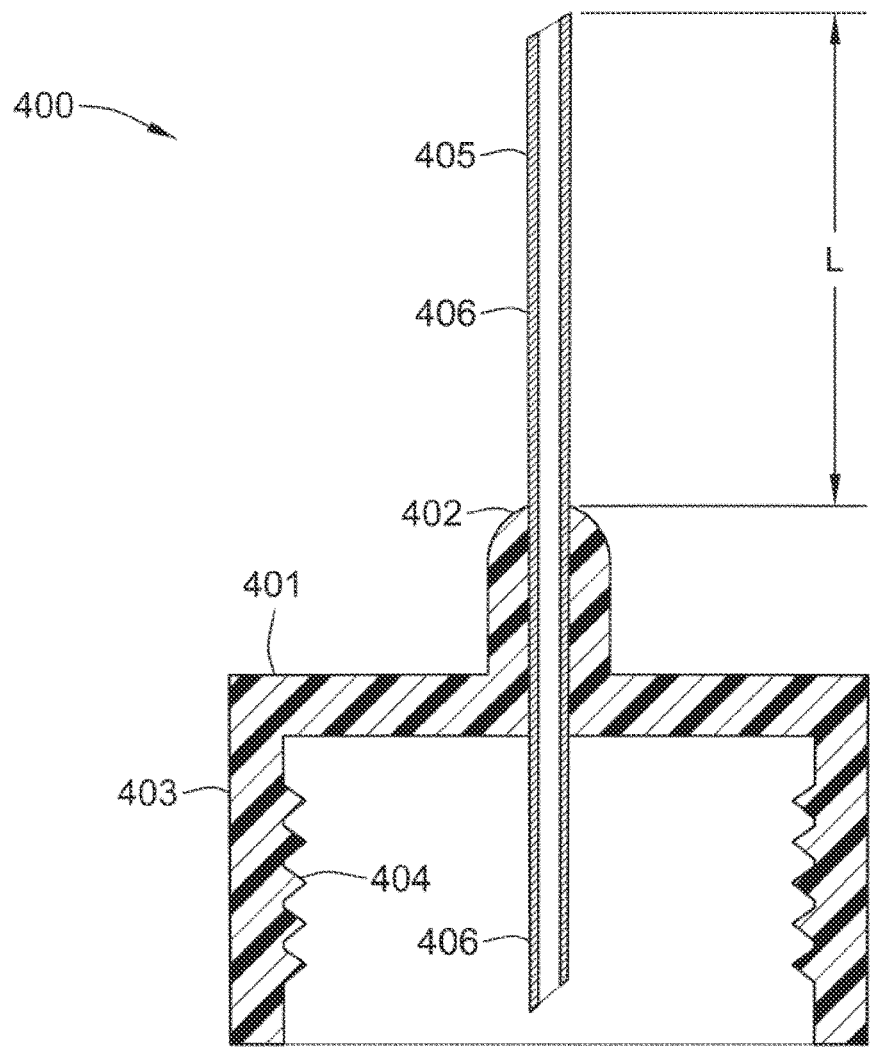
FIG. 6 illustrates a needle assembly that may be mounted on a distal end of the delivery device.
Figure 7:
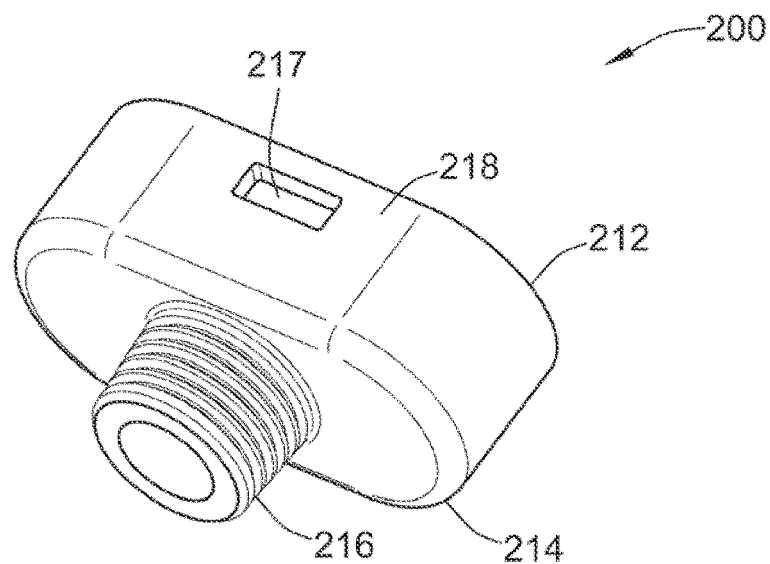
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 402 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 406 of the needle assembly 400 protrudes from an opposite side of the circular disc so that it is concentrically surrounded by the sleeve 403. In one needle assembly arrangement, the second or proximal piercing end 406 may be shorter than the sleeve 403 so that this sleeve to some extent protects the pointed end of the back sleeve. The needle cover cap 420 illustrated in FIGS. 4 and 5 provides a form fit around the outer surface 403 of the hub 401.

Referring now to FIGS. 4 to 11, one preferred arrangement of this interface 200 will now be discussed. In this one preferred arrangement, this interface 200 comprises:
 a. a main outer body 210,
 b. an first inner body 220,
 c. a second inner body 230,
 d. a first piercing needle 240,
 e. a second piercing needle 250,
 f. a valve seal 260, and
 g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213a and a second rib 213b. This first rib 213a is also illustrated in FIG. 10. These ribs 213a and 213b are positioned along the inner surface 215 of the wall 218 of the outer body 210 and create a form fit or snap lock engagement with cooperating grooves 224a and 224b of the first inner body 220. In a preferred arrangement, these cooperating grooves 224a and 224b are provided along an outer surface 222 of the first inner body 220.

Figure 8:
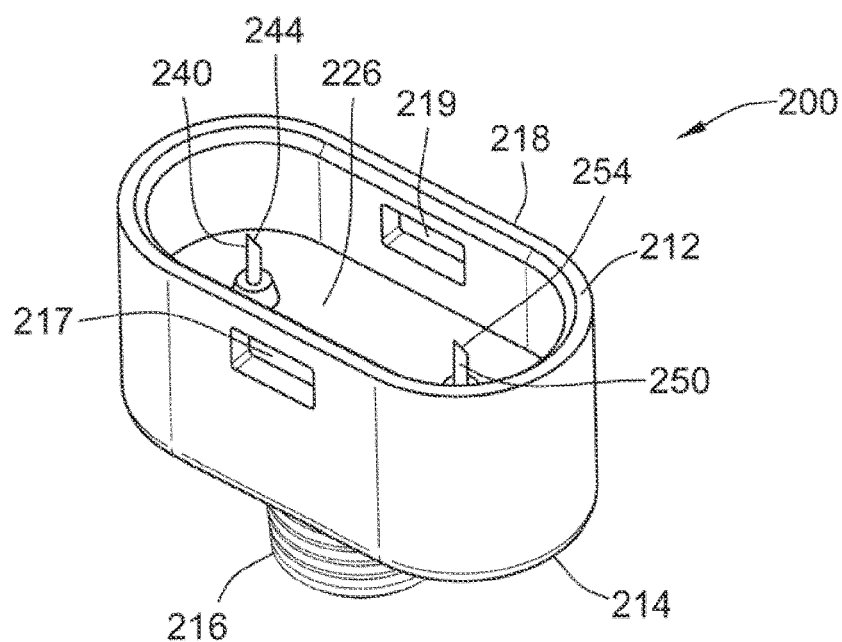
FIG. 8 illustrates another perspective view of the dispense interface illustrated in FIG. 4.
Figure 9:
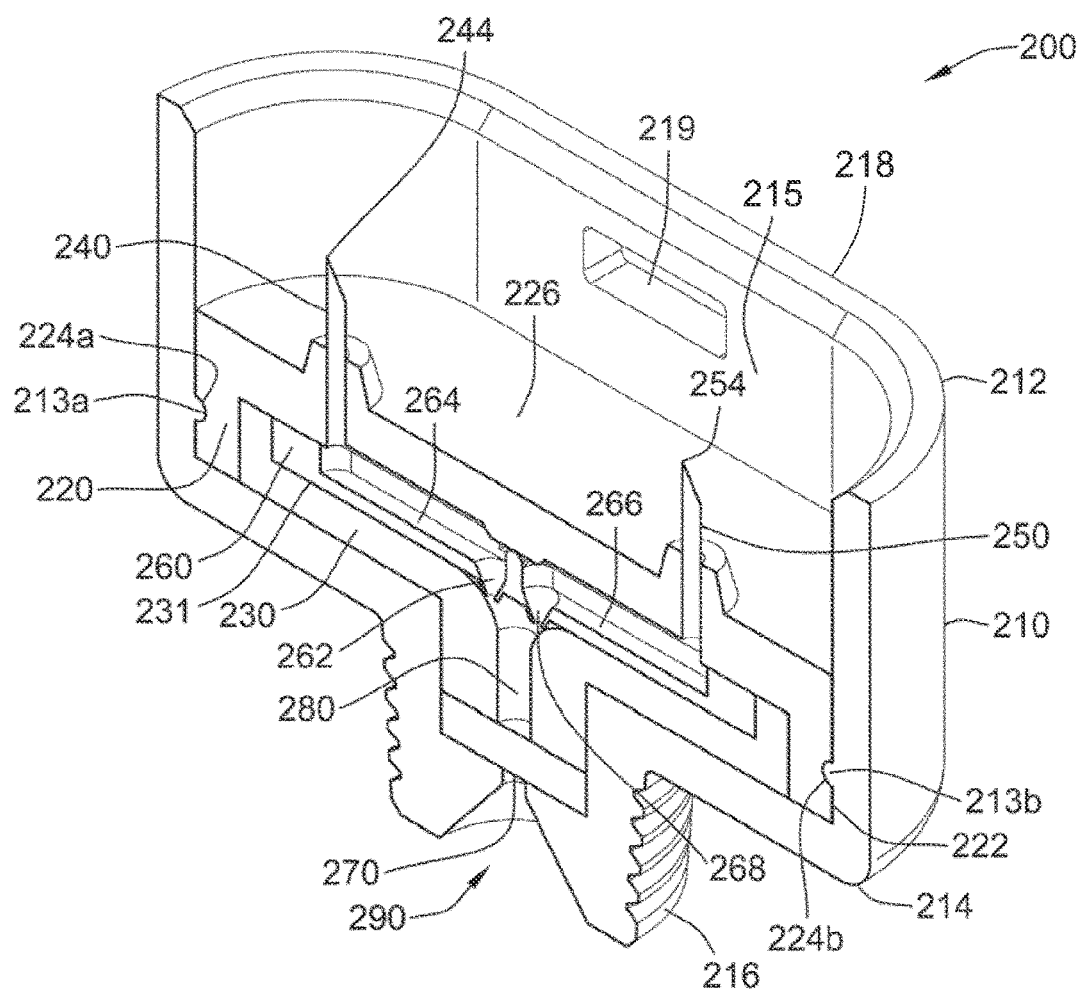
FIG. 9 illustrates a cross-sectional view of the dispense interface illustrated in FIG. 4.
Figure 10:
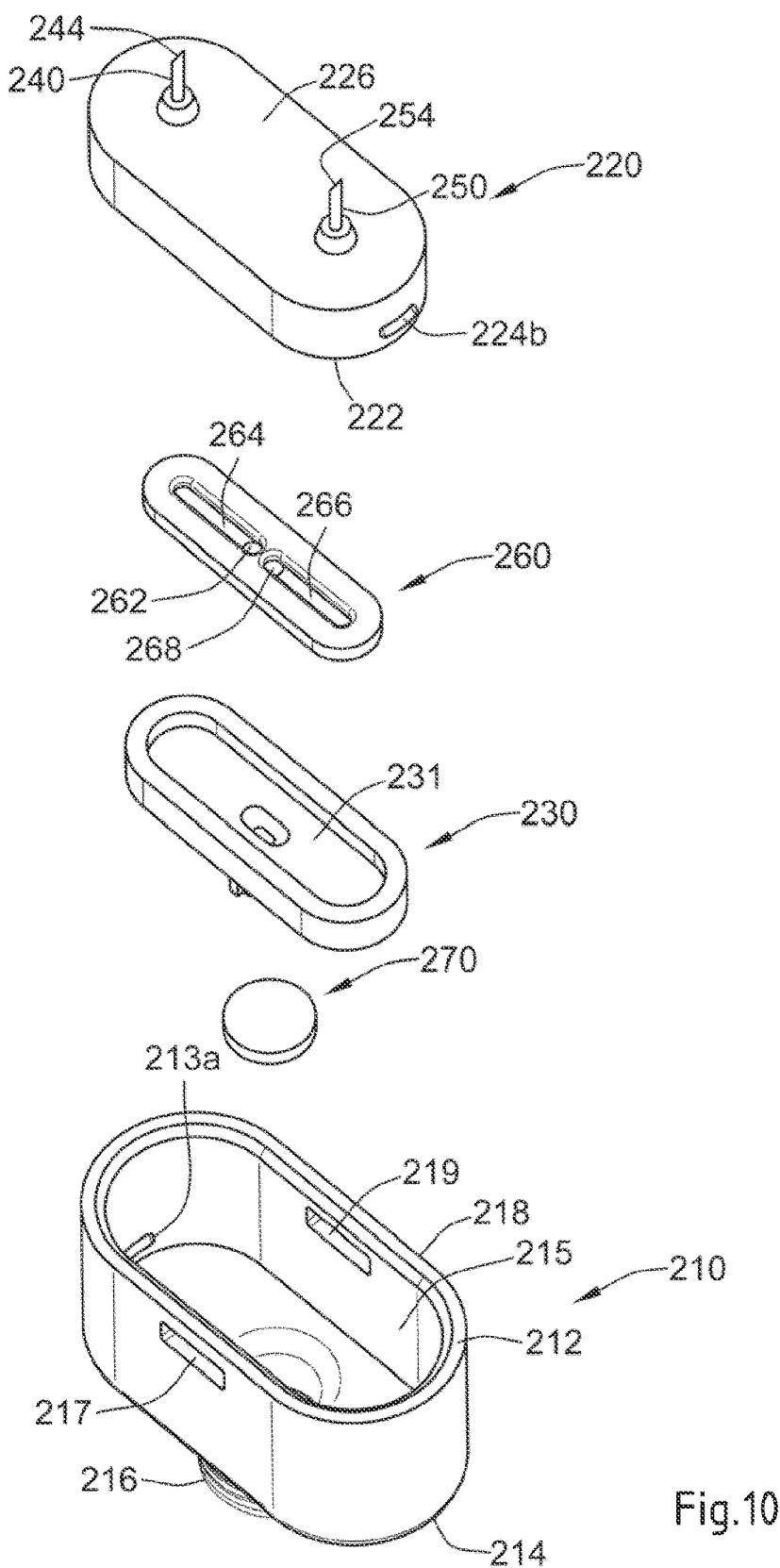
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
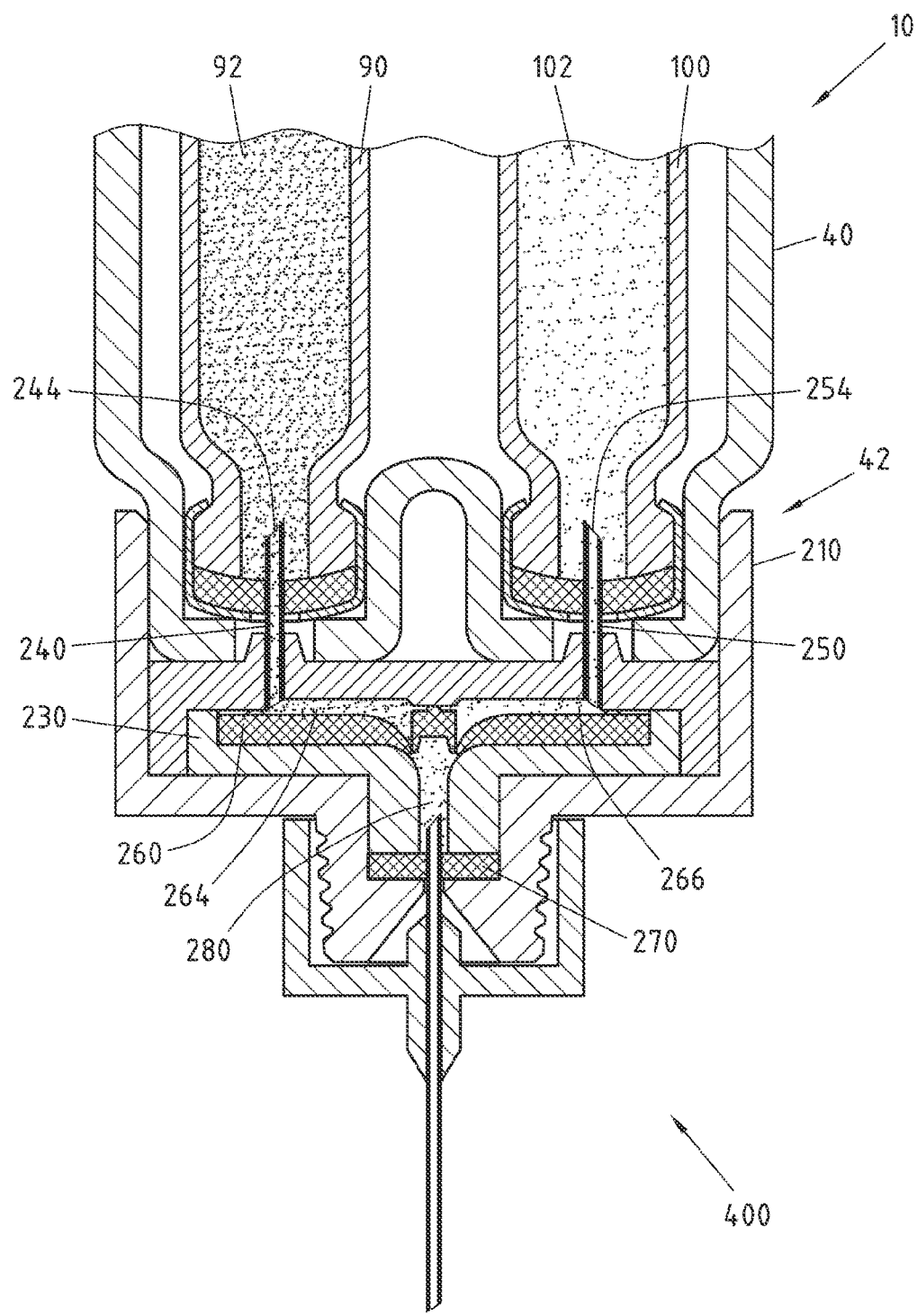
FIG. 11 illustrates a cross-sectional view of the dispense interface and needle assembly mounted onto a drug delivery device, such as the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

In the following embodiments of the present invention will be described in detail with reference to FIGS. 12 to 17.

In an example embodiment, the dispense interface can include a lockout mechanism. Such a lockout mechanism can prevent the dispense interface from being reattached to the drug delivery device once the interface has been initially removed from the device. Such a feature may help reduce the possibility of contamination as well as prevent possible blunting of the dispense interface needle injections ends. These features are described in greater detail below.

Figure 12:
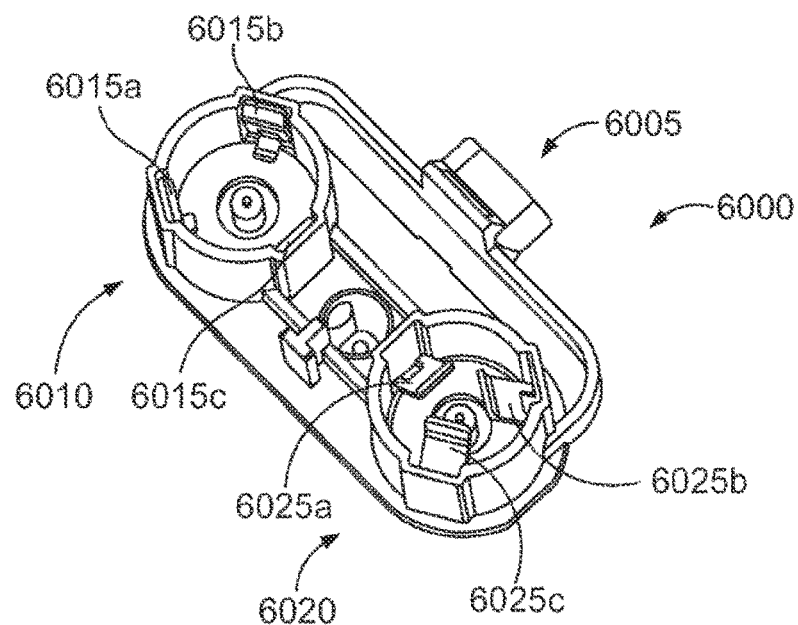
FIG. 12 illustrates a perspective view of a dispense interface comprising a lockout element.

FIG. 12 illustrates a perspective view of a dispense interface 6005 comprising a lockout element 6000. Specifically, FIG. 12 illustrates a perspective view of the proximal end of the dispense interface 6005 comprising a lockout element 6000 that comprises a first and a second button spring 6010, 6020. As illustrated, the button springs 6010, 6020 may comprise a version of an over-centering wing spring. In one arrangement, each of the button springs 6010, 6020 comprise three winged tabs which can function to lockout the lockout element 6000 and prevent the dispense interface 6005 from re-use. For example, first button spring 6010 may comprise three winged tabs 6015a, 6015b, 6015c and second button spring may comprise three wing tabs 6025a, 6025b, 6025c. The first and second springs 6010, 6020 are generally dome shaped so as to provide an over-centering force.

Figure 13:
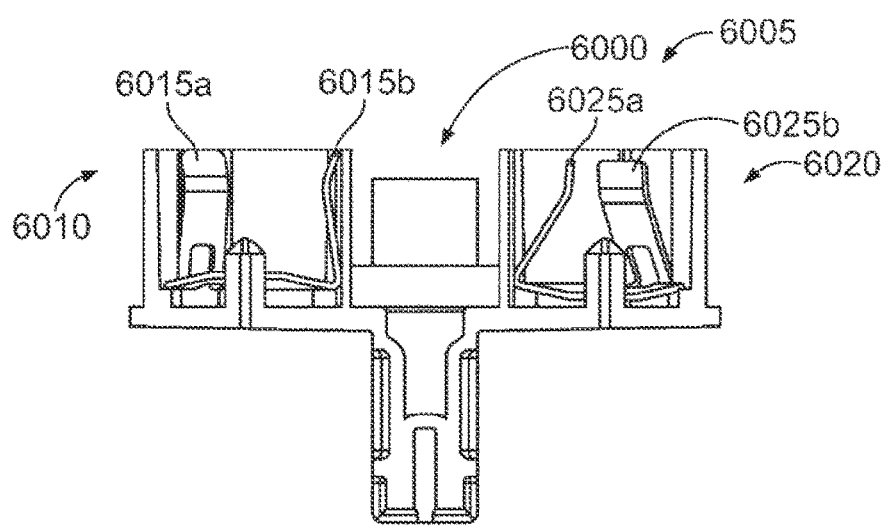
FIG. 13 illustrates a cross-sectional view of the dispense interface illustrated in FIG. 12.

FIG. 13 illustrates a cross sectional view of the dispense interface 6005 and lockout element 6000 illustrated in FIG. 12. As illustrated, one side of the dispense interface 6005 is shown with the button spring 6010 in the receptive condition. That is, the three winged tabs 6015a, 6015b, 6015c of button spring 6010 reside in an open position so as to receive a distal end of a cartridge from the drug delivery device. The other side of the dispense interface 6005 is shown where the second button spring 6020 resides in the locked condition, i.e., where the three winged tabs 6025a, 6025b, 6025c reside in a locked position and therefore would not be able to received a distal end of a cartridge form the drug delivery device.

Figure 14:
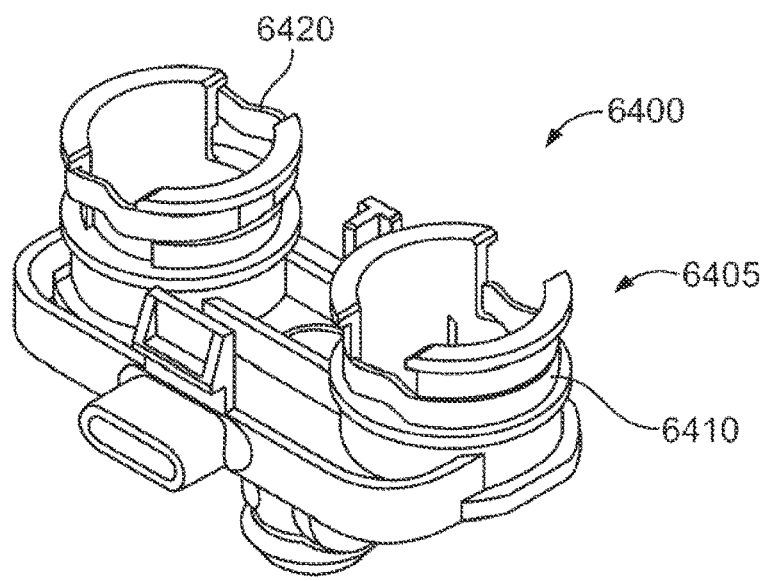
FIG. 14 illustrates a perspective view of an alternative arrangement of a dispense interface comprising a lockout element.

FIG. 14 illustrates a perspective view of an alternative arrangement of a dispense interface 6405 comprising a lockout element arrangement 6400. In this arrangement, the lockout element arrangement 6400 comprises a first circlip spring 6410 and a second circlip spring 6420.

Figure 15:
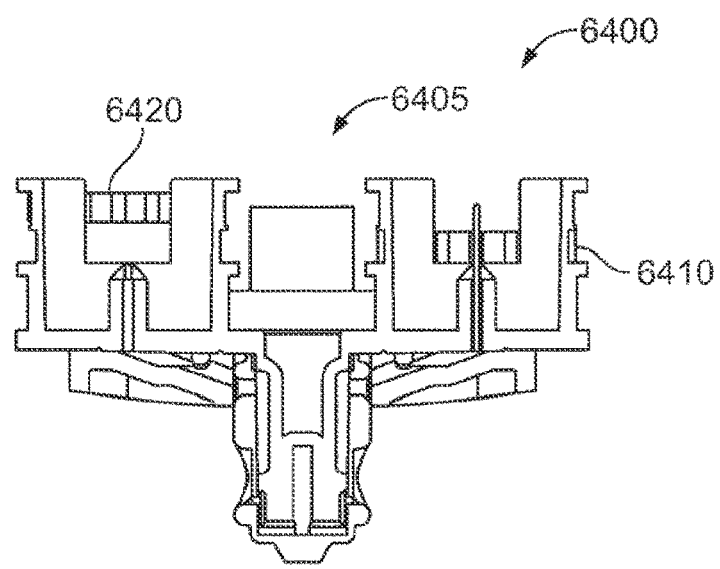
FIG. 15 illustrates a cross-sectional view of the dispense interface illustrated in FIG. 14.

FIG. 15 illustrates a cross sectional view of the dispense interface 6405 and lockout element arrangement 6400 illustrated in FIG. 14. In this particular arrangement, it is conceptually similar to the lockout element 6000 illustrated in FIGS. 12-13 and discussed herein. In the arrangement illustrated in FIGS. 14-15, a pair of radial clips 6410, 6420 are held open within a large diameter channel of the dispense interface 6405. A pair of cartridge bosses on the drug delivery device (not illustrated) may be received into these clips 6410, 6420. When the dispense interface 6405 comprising the lockout element 6400 is fitted onto the cartridge bosses, the clips are contacted and are shunted forwards (in a distal direction) into a second channel which is on a smaller diameter. In this position where the clip resides in a second channel of smaller diameter, the clips 6410, 6420 are activated. Thereafter, once the drug delivery device is removed, the clips spring inwards. Bend portions of the clips deflect sufficiently inwards to shrink the effective receptive boss diameter, forming a lockout condition of the clips. For example, as illustrated in FIG. 15, the first clip spring 6410 remains in the locked condition while the second clip spring 6420 remains in the receptive condition.

Figure 16:
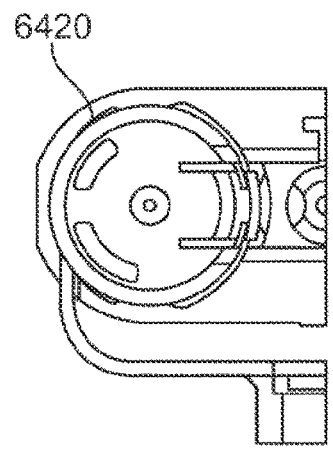
FIG. 16 illustrates a cross-sectional view of a portion of the dispense interface illustrated in FIG. 14
Figure 17:
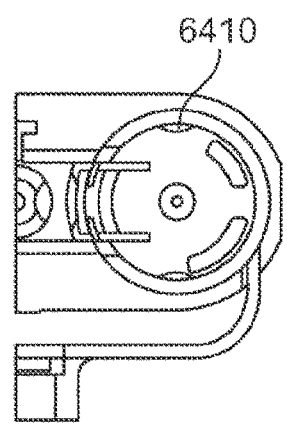
FIG. 17 illustrates a cross-sectional view of another portion of the dispense interface illustrated in FIG. 14.

FIGS. 16 and 17 illustrate portions of the dispense interface 6405 illustrated in FIG. 15. Specifically, FIG. 16 illustrates a top perspective view of the second clip 6420 of the lockout element 6400 residing in the receptive condition. Specifically, FIG. 17 illustrates a top perspective view of the first clip 6410 of the lockout element 6400 illustrated in the locked condition with the bend portions of the clips deflecting sufficiently inwards.

Alternative embodiments for holding the spring in an initially open condition could also be used. As just one example, a tab feature which initially sits between the clip ends may be deflected away from the clip mouth during fitment of the dispense interface onto the drug delivery device.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(02)25, Asp28] Exendin-4(1-39)-Lys6-NH2,
H-des Asp28 Pro36, Pro37, Pro38 [Trp(02)25] Exendin-4(1-39)-NH2,
H-(Lys)6-des Pro36, Pro37, Pro38 [Trp(02)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(0)14, Trp(02) 25, Asp28] Exendin-4(1-39)-NH2, des Pro36, Pro37, Pro38 [Met(O)14, Trp(02)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. An apparatus comprising:
a dispense interface for use with a drug delivery device, the dispense interface comprising a lockout element, the lockout element comprising at least one tubular stub and at least one spring component removeably maintained in a respective first position such that when the dispense interface is first attached and then removed from said drug delivery device, where each tubular stub has a first diameter channel and a smaller second diameter channel and each spring component moves into a respective second position, which respective second position prevents said dispense interface from being reattached to a drug delivery device, wherein each spring component comprises a respective circlip spring, and wherein each circlip spring is maintained in the first diameter channel when in the first position, where each circlip moves to the second diameter channel through direct contact with the drug delivery device and moves to the second position when contact with the drug delivery device is removed.

2. The apparatus according to claim 1, wherein each circlip spring is configured to be shunted forwards into the respective second diameter channel which is on a smaller diameter than the respective first diameter channel when the dispense interface is attached to said drug delivery device.

3. The apparatus according to claim 2, wherein each circlip spring is configured to spring inwards in a radial direction when said dispense interface is removed from said drug delivery device.

4. The apparatus according to claim 3, wherein a portion of each circlip spring is configured to deflect sufficiently inward to shrink an effective receptive diameter to prevent said dispense interface from being reattached to the drug delivery device.

5. The apparatus according to claim 1, wherein each circlip spring is maintained in the respective first position by a respective tab.

6. The apparatus according to claim 5, wherein each circlip spring is configured to move into a respective locked condition upon deflection of the respective tab during attachment of the dispense interface to said drug delivery device and subsequent detachment of the dispense interface from the drug delivery device.

* * * * *